United States Patent [19]

Follmer et al.

[11] Patent Number: 5,728,065
[45] Date of Patent: Mar. 17, 1998

[54] SELF-VENTING ELASTOMERIC BALLOON CATHETER

[75] Inventors: Brett A. Follmer, Sunnyvale; William S. Tremulis, Redwood City; Erin McGurk, Palo Alto, all of Calif.

[73] Assignee: Medtronic, Inc., Minneapolis, Minn.

[21] Appl. No.: 667,536

[22] Filed: Jun. 21, 1996

[51] Int. Cl.$^6$ .................................................. A61M 25/00
[52] U.S. Cl. .................................................. 604/96; 606/194
[58] Field of Search .................................. 604/96, 97–103, 604/118; 606/191–194

[56] References Cited

U.S. PATENT DOCUMENTS

| | | | |
|---|---|---|---|
| 4,323,071 | 4/1982 | Simpson et al. | 128/343 |
| 4,413,989 | 11/1983 | Schjeldahl et al. | 604/96 |
| 4,638,805 | 1/1987 | Powell | 128/344 |
| 4,692,200 | 9/1987 | Powell | 156/289 |
| 4,715,378 | 12/1987 | Pope, Jr. et al. | 128/344 |
| 4,810,455 | 3/1989 | Pope, Jr. et al. | 264/273 |
| 4,813,934 | 3/1989 | Engelson et al. | 604/99 |
| 4,821,722 | 4/1989 | Miller et al. | 128/344 |
| 5,049,130 | 9/1991 | Powell | 604/96 |
| 5,100,385 | 3/1992 | Bromander | 604/99 |
| 5,176,698 | 1/1993 | Burns et al. | 606/192 |
| 5,209,728 | 5/1993 | Kraus et al. | 604/96 |
| 5,256,143 | 10/1993 | Miller et al. | 604/96 |

*Primary Examiner*—John D. Yasko
*Attorney, Agent, or Firm*—Townsend and Townsend and Crew LLP

[57] ABSTRACT

A balloon catheter comprises a catheter body having an elastomeric balloon at its distal end. The balloon has a small diameter vent hole disposed near its distal end. The balloon catheter may be prepared by flushing an inflation lumen and the interior of the balloon with a suitable liquid flushing medium, where the balloon is inflated by the flushing medium beginning at its proximal end and moving toward its distal end.

30 Claims, 5 Drawing Sheets

SELF-VENTING ELASTOMERIC BALLOON CATHETER

BACKGROUND OF THE INVENTION

1. Field of the Invention

The present invention relates generally to medical balloon catheters and methods for their deployment. More particularly, the present invention relates to elastomeric balloon catheters having small diameter holes formed therein for venting of entrapped gases.

Medical catheters exist for a wide variety of purposes, including diagnosis, interventional therapy, drug delivery, drainage, perfusion, and the like. Catheters for each of these purposes can be introduced to numerous target sites within a patient's body by guiding the catheter through the vascular system, and a wide variety of specific catheter designs have been proposed for different uses.

Small diameter tubular access catheters are presently being used for diagnostic and interventional neurological techniques, such as the imaging and treatment of aneurysms, tumors, arteriovenous malformations, fistulas, and the like. The neurological vasculature places a number of requirements on the catheters which are to be employed. The primary requirement is size. The blood vessels in the brain are frequently as small as several millimeters, or less, requiring that the catheters have an outside diameter as small as one French (1F; 0.33 millimeters). In addition to small size, the brain vasculature is highly tortuous, requiring that neurological catheters be very flexible, particularly at their distal ends, to pass through the regions of tortuosity.

Of particular interest in the present invention, small diameter access catheters may be provided with elastomeric balloons near their distal ends for a variety of purposes. For example, the elastomeric balloons may provide selective occlusion of the vessel in which the catheter is present to permit or facilitate the release of fluids, embolic coils, and other devices and agents. Such balloons will be inflated with liquid media, such as contrast media, saline, or mixtures thereof. In case of balloon rupture, it is important that any gases which may have been initially entrapped within the balloon be flushed or vented from the balloon prior to use. Inadvertent balloon rupture and release of gases can cause arterial embolism which is a particular problem when the catheters are used in the vasculature of the brain.

A variety of structures have been proposed for self-venting of balloon catheters. For example, U.S. Pat. No. 4,638,805 describes a catheter having a small tube at its distal end for releasing entrapped gases as the balloon is inflated with liquid medium. While functional, use of such a vent tube is disadvantageous since it remains open at all times, thus permitting gases to re-enter the balloon after initial flushing. Similarly, U.S. Pat. Nos. 4,821,722 and 5,256,143, disclose angioplasty balloon catheters having a plurality of fixed diameter holes formed near their distal end. As angioplasty balloons are typically formed from non-distensible materials, the holes formed in these balloons will remain open at all times, and the provision of such a large number of balloons can weaken the balloon wall.

For these reasons, it would be desirable to provide improved self-venting balloon catheters. In particular, it would be desirable to provide self-venting mechanisms intended for use with elastomeric balloons, where the vents will selectively and preferentially open while the balloon is being flushed, but will at least partially close during normal use and when the balloon is deflated. Such balloon vents should be suitable for use with virtually any medical balloon catheter having an elastomeric balloon, and should particularly be compatible with elastomeric balloons on very small catheters of the type used in neurological interventions.

2. Description of the Background Art

U.S. Pat. Nos. 4,821,722 and 5,256,143, describe angioplasty balloon catheters having a plurality of vent holes formed in the balloon. The nature of the balloon of the '722 and '143 patents is described in U.S. Pat. No. 4,323,071. Other patents describing self-venting balloon catheters include U.S. Pat. Nos. 4,692,200; 4,715,378; 4,810,455; and 5,100,385. Balloon catheters having vent paths which are selectively blocked by a guidewire or similar element are disclosed in U.S. Pat. Nos. 4,413,989; 4,813,934; 5,176,698; and 5,209,728. U.S. Pat. No. 5,049,130, describes a vascular catheter having a rigid distal housing having an elastomeric collar at its proximal end that permits selective venting.

Balloon catheters and elastomeric and non-distensible balloons are described in copending application Ser. Nos. 08/562,565 and 08/344,183, assigned to the assignee of the present invention, the full disclosures of which are incorporated herein by reference.

SUMMARY OF THE INVENTION

A balloon catheter constructed in accordance with the principles of the present invention comprises a catheter body having a proximal end, a distal end, and at least one inflation lumen extending from the proximal end to near the distal end. An elastomeric balloon is disposed over the catheter body near its distal end and receives inflation media from the inflation lumen. At least a portion of the balloon comprises an elastomeric membrane having at least one vent hole therethrough. Preferably, the vent hole is located near the distal end of the balloon, and the balloon is sized so that it remains constricted over the catheter body when uninflated. When the balloon is thus constricted, the interior opening of the vent hole will be covered by the catheter body so that air or other gases cannot enter the balloon. The inflation lumen is preferably disposed at or near the proximal end of the balloon so that introduction of a liquid inflation medium will cause liquid to advance through the balloon in a front, resulting in progressive expansion of the balloon from the proximal end to the distal end. In this way, any air or other gases entrapped within the balloon will be caused to move distally toward the vent hole, thus providing for flushing of gases from the interior of the balloon.

The vent hole will be sized to permit the release of gases but to inhibit the release of liquids, such as the inflation medium which is used to inflate the balloon. Usually, the vent hole will have a maximum width in range from 0.1 mm to 0.25 mm when the balloon is uninflated. When inflated to a pressure of about 0.5 atm, the size of the vent hole will increase, typically to a maximum width in range from 0.01 mm to 0.5 mm, usually in the range from 0.05 mm to 0.35 mm. The ability of the vent hole to expand with the elastomeric balloon is a significant advantage over prior vent holes which had been formed in conventional non-distensible angioplasty balloons. By expanding the vent hole, the ability to flush gases can be enhanced when the catheter is being prepared prior to use. In particular, the balloon may be inflated to a pressure well over that at which it will normally be employed. Thus, very small vent holes can be initially formed in the uninflated balloon material, where the vent holes are enlarged to release gasses and even flush liquid from the balloons during the preparation stage. When the balloon is deflated, the cross-sectional area of the vent hole will decrease to the smaller size, thus enhancing the ability to maintain liquid at lower operating pressures. Additionally, when the elastomeric balloon material collapses against the catheter body, the vent hole is effectively closed so that gases from the environment cannot re-enter the balloon after it is initially flushed and prepared.

The elastomeric balloon will be composed at least partially of an elastomeric or blended elastomeric material, typically comprising an elastomeric membrane material, such as latex, silicone rubber, or synthetic material, such as a polyurethane or the like. Preferred is the use of polyurethane. While the balloon will usually be composed entirely of a single material and will usually have a uniform thickness, it will be possible to prepare composite materials including layers or regions formed from differing materials and further possible to provide for regions of varying thickness or other non-uniformities. At least the portion of the balloon which includes the vent hole, however, will be elastomeric so that it possess the features described above.

A preferred balloon catheter assembly comprises an elastomeric balloon having a proximal end and a distal end, where both the proximal end and distal ends are circumferentially attached to the catheter body to define spaced-apart hinge regions. In its uninflated configuration, the balloon will lie closely constricted over the catheter body with the hinge regions lying relatively flat. As the balloon is inflated, the proximal hinge region will first deflect radially outwardly from the catheter body as the balloon expands radially. The vent hole will be located near the distal hinge region, typically being within 0.1 mm to 1 mm of the hinge, and will open as the balloon begins to expand near the distal hinge. As the vent hole opens, the gases which have advanced together with the front of balloon expansion medium, will pass outwardly through the vent hole. By inflating the balloon with liquid medium above a certain threshold pressure, typically about 0.5 atm, the vent hole will be expanded sufficiently to permit flushing of liquid therethrough. The ability to flush liquid through the vent hole helps assure that previously entrapped gases will be removed. After flushing is complete, the flushing liquid is aspirated or otherwise removed from the balloon, thus closing the vent hole as described above.

In the exemplary embodiment of the balloon catheter, the catheter body comprises an inner tubular member and an outer tubular member. The outer tubular member is received over the inner tubular member, typically in a coaxial fashion, so that an annular inflation lumen is formed therebetween. The proximal end of the elastomeric balloon is attached near the distal end of the outer tubular member, and the distal end of the balloon is attached near the distal end of the inner tubular member. In this way, the inflation lumen opens immediately at the proximal end of the balloon.

The present invention further provides inflation systems for balloon catheters. The inflation systems include balloon catheters, generally as described above, and a tubular constraining member having a lumen for receiving the elastomeric balloon of the balloon catheter. The lumen is sized so that it will limit radial expansion of the balloon to a pre-selected size, typically a diameter which corresponds generally to the maximum intended inflation diameter for the balloon. In this way, the elastomeric balloon can be inflated to a pressure over its normal maximum pressure to enhance opening of the vent hole and rapid flushing of the balloon.

A method according to the present invention comprises providing a balloon catheter having an elastomeric balloon with a vent hole in the balloon. The balloon is inflated with a liquid medium to resiliently expand the balloon and vent gases trapped in the balloon through the vent hole. Usually, the vent hole is disposed near a distal end of the balloon and the balloon is inflated so that it progressively opens from the proximal end to the distal end. In this way, entrapped gases are caused to move toward the vent (i.e., flushed from the interior of the balloon) as the balloon is inflated. Additionally, inflation of the balloon will cause the cross-sectional area of the vent hole to increase as it expands, thus enhancing the ability to vent gases from the balloon and flush liquid through the vent hole. Usually, the elastomeric balloon is inflated within a tubular constraining member, where the constraining member has a tubular lumen with a diameter which is from 25% to 100% of the nominal maximum inflation diameter of the balloon. The balloon will typically be inflated to a pressure in the range from 1 psi to 60 psi, usually 6 psi to 15 psi and/or with a liquid volume in the range from 0.03 ml to 0.15 ml.

DESCRIPTION OF THE SPECIFIC EMBODIMENTS

According to the present invention, balloon catheters are provided comprising a catheter body having an elastomeric balloon at a distal thereof. The catheter body may comprise any of a variety of conventional catheter body constructions for use in known medical procedures. Usually, although not necessarily, procedures will be intravascular procedures performed in the peripheral, visceral, and coronary vasculature. Exemplary procedures include occlusion, e.g, placement of embolic coils and materials, angiography, aneurysm repair, treatment of vasospasms, and the like.

The catheter body will have a proximal end, a distal end, and at least one inflation lumen extending generally from the proximal end to the distal end. The inflation lumen will be used for supplying a liquid inflation medium to the elastomeric balloon which is secured at or near the distal end of the catheter body. Usually, a proximal hub will be attached to the proximal end of the catheter body and provide suitable ports for passing guidewires providing inflation medium to the inflation lumen, and the like. In the exemplary embodiment described in more detail below, a catheter body has a coaxial construction including an inner tubular member, and an outer tubular member, where the inflation lumen is formed in the annular space therebetween. The inner tubular member further includes at least one additional lumen for passing the catheter over a guidewire.

The dimensions and materials of construction for the catheter body will be conventional for medical catheters. Typically, the catheter body will have a length in the range from 50 cm to 250 cm, more usually from 100 cm to 200 cm. The outer diameter of the catheter body may be from 1 mm (3 French), or below up, to 4 mm (12 French), or above. The self-venting mechanism of the present invention is particularly useful in very small catheters, typically having a diameter of 2 French or below, often 1 French or below, for use in neurological and other interventions. An exemplary construction for such catheter is set forth in detail below.

The elastomeric balloon may be composed of any biocompatible elastomeric material of a type conventionally used in medical devices. Exemplary materials include latex, silicone rubbers, polyurethanes, and the like. The preferred balloon is composed of polyurethane, and will have a length in the range from 3 mm to 100 mm, and outer diameter (when inflated at a target site to 0.5 atm) in the range from 2 mm to 20 mm. The thickness of the balloon wall or membrane will typically be in the range from 0.025 mm to 0.25 mm when the balloon is uninflated. Such elastomeric balloons will typically have a spherical or spheroidal profile when inflated. When deflated, the balloons will lie closely over the outer surface of the catheter body and thus will typically have a cylindrical profile.

Figure 1:
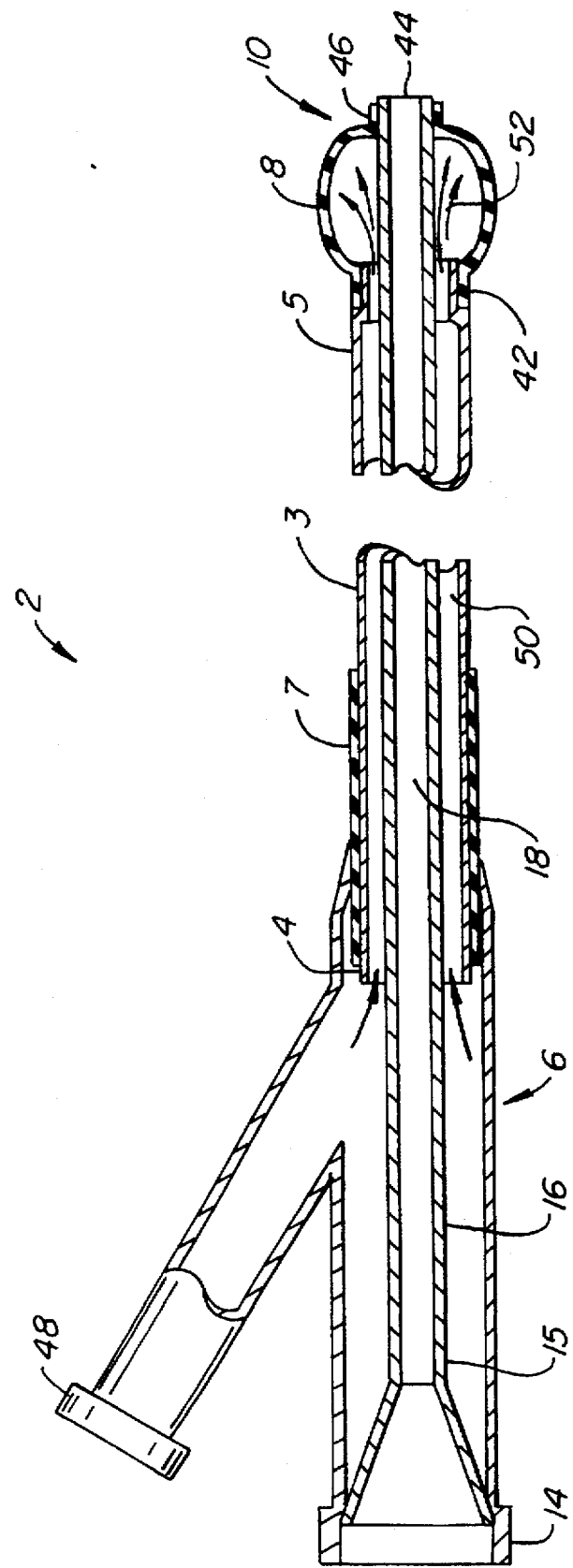
FIG. 1 is a cross-sectional side view showing a balloon catheter constructed in accordance with the principles of the present invention.

FIG. 1 illustrates a simplified side view of a balloon catheter made according to the invention. Balloon catheter 2 includes an outer tubular member (sheath) 3 made of, for example, Pebax®, a polyamide polyether block copolymer, having a proximal end 4 and a distal end 5. A hub assembly 6 is mounted to the proximal end 4 through a strain relief collar 7. An annular, elastomeric balloon 8 is secured to distal end 5 of outer tubular member 3 and to an inner tubular member 16 disposed coaxially within the outer tubular member as will be discussed in more detail below. Hub assembly 6 includes a connector 14 coupled to the proximal end 15 of inner tubular member 16.

The exemplary inner tubular member 16 will typically have a length in the range from about 40 cm to 200 cm, usually having a length in the range from about 60 cm to 175 cm. The outside diameter of the outer tubular member will typically be in the range from about 0.33 mm (1 F) to 4 mm (12 F), usually being in the range from about 0.66 mm (2 F) to about 2.66 mm (8 F). The inner tubular member 16 of the catheter body will define an inner lumen 18 typically having a diameter in the range from about 0.1 mm to 3.6 mm, usually being in the range from about 0.3 mm to 2.5 mm, with catheters having larger outside diameters usually having larger lumen diameters. For the preferred microcatheters of the present invention, the inner tubular member 16 will have a length in the range from about 80 cm to 150 cm, an outside diameter in the range from about 0.66 mm to 1.75 mm, and an inside diameter in the range from about 0.375 mm to 1.07 mm.

The catheter body usually will be straight along all or most of its length. By "straight" it is meant that the catheter body will assume a straight or linear configuration, when free from external bending forces. The catheter body, however, will be highly flexible so that it will be able to pass through the tortuous regions of a patient's vasculature, as described in more detail herein below. In some cases, the catheter body may have a shaped distal end including curves and bends which are selected to facilitate introduction and placement of the catheter (usually over a separate guidewire) in the vascular system. A particular geometry of curves and/or bends may be selected to accommodate the intended use of the catheter.

Balloon 8 is bonded distal end 5 of outer tubular member 3. Distal end 5 is necked-down to reduce outside diameter after annular end 42 of balloon is attached. Balloon 8 is mounted to end 5 of the outer tubular member 3 using an adhesive such as an RTV silicone adhesive, for example Loctite 5140 or Nusil Technology R-1140, or a UV curing adhesive. A distal annular edge 46 of elastomeric balloon 8 is bonded to tip 44 of the inner tubular member 16 using the same or a similar adhesive as used with end 42.

Hub assembly 6 includes an injection port 48 fluidly coupled to an inflation passageway 50 defined between outer tubular member 3 and inner tubular member 16. An inflation medium, such as contrast fluid, saline, etc., can be injected through port 48, into passageway 50 and out through an annular exit opening 52 defined between distal end 5 of sheath 3 and distal region 24 of catheter body 12. Doing so causes balloon 8 to expand to either partially or totally occlude the particular vessel within which the balloon has been placed. Total occlusion of the vessel can be desired for, for example, diagnostic purposes or to permit injection of saline to promote successful use of endoscopic devices. Partial occlusion can be useful when injecting particles, tissue adhesives or coils, when placing detached balloons and when conducting diagnostic procedures and other therapeutic procedures.

Balloons having minimum and maximum diameters from about 4 to 14 mm can be used with inner catheter/outer sheath sizes from about 3.2 F/5.5 F to about 7 F/9.5 F. Balloons having minimum and maximum diameters from about 2 to 7 mm can be used with inner catheter/outer sheath sizes from about 1 F/3 F to about 3.2 F/6.5 F.

Although not shown in the figures, it is preferred to secure inner tubular member 16 to outer tubular member 3 at several places, typically three, in addition to their distal ends (through balloon 8) and their proximal ends (through injection port assembly 16). This can be accomplished by staking outer sheath 3 against inner catheter at several positions in a manner not to seal off passageway 50. Alternatively, outer layer 34 can be made with raised buttons or beads of material extending from the outer surface of outer layer 34; after assembly, outer tubular member 3 can be heat-sealed to outer layer 34 of inner tubular member 16 at the beads or buttons, again while maintaining free fluid flow along passageway 50.

Outer tubular member 3 can be further modified for particular uses. For example, small perfusion ports or holes can be formed near distal end 5 to facilitate liquid perfusion, e.g., drug delivery, using catheter 2. Coatings such as hydrophilic, anti-thrombogenic, low-friction, hydrophobic, and other, coatings can be placed over the outer surface of the outer tubular member 3 to enhance its use for particular applications. Additionally, distal end 5 can be formed into a desired geometry.

As described thusfar, the construction of balloon catheter 2 is generally the same as that described in copending application Ser. Nos. 08/562,565 and 08/344,183, the disclosures of which have previously been incorporated herein by reference. The present invention is an improvement over the catheters described in these copending applications. In particular, the present invention provides for a vent hole 70 within the balloon 8, typically disposed at the distal end of the balloon immediately proximal to the annular or circumferential connection 46 of the balloon to the inner tubular member 16. The vent hole 70 formed in the elastomeric balloon selectively opens and closes to facilitate venting of gases from the balloon, as will be described in more detail below. Preferably, only a single vent hole 70 will be provided but two or more could be used so long as the mechanical integrity of the balloon is not compromised.

Figure 2:
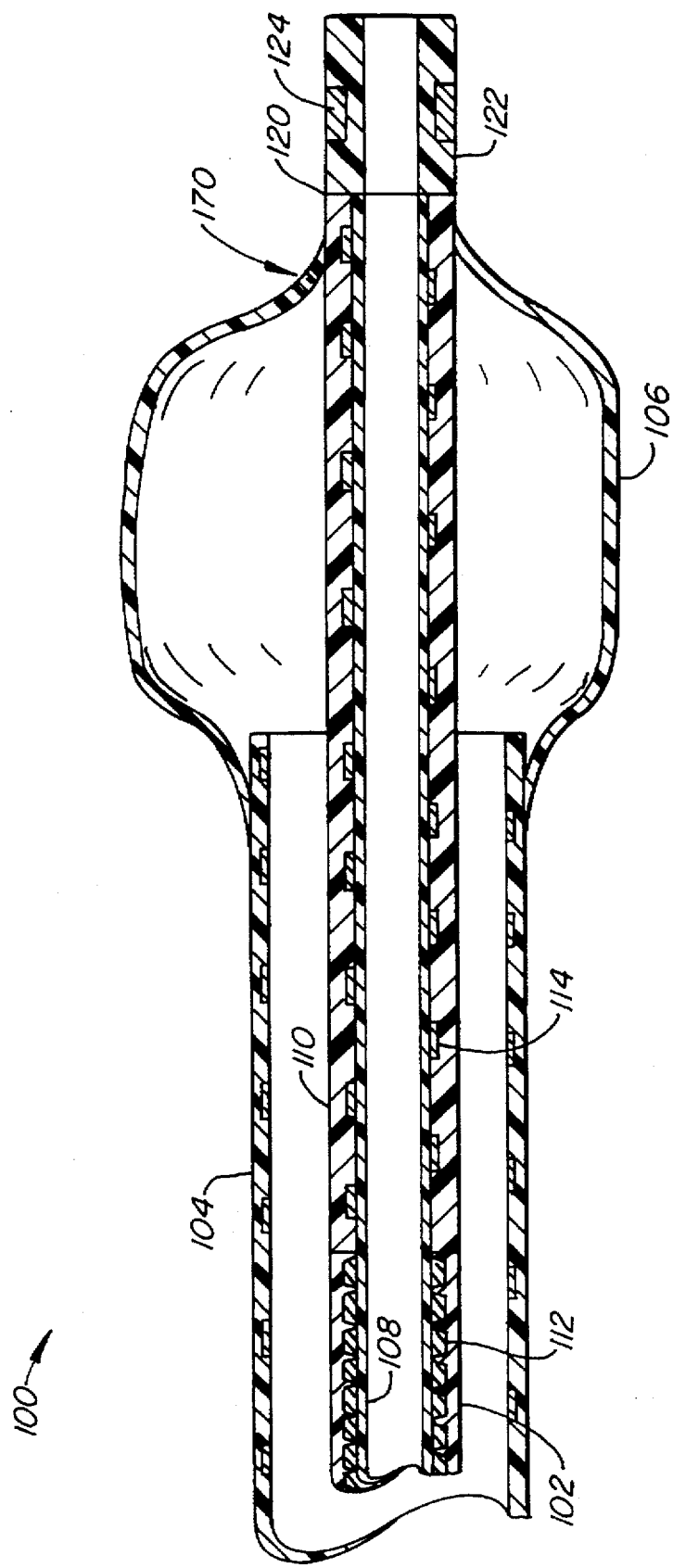
FIG. 2 is a detailed side view of the distal end of the catheter similar to the catheter of FIG. 1.

A catheter 100 having a presently preferred construction is illustrated in FIG. 2. Balloon catheter 100 comprises an inner tubular member 102, an outer tubular member 104, and an elastomeric balloon 106. Portions of the catheter 100 proximal to those illustrated may be identical to catheter 2 illustrated in FIG. 1.

The inner tubular member 102 comprises inner layer 108 and a soft outer layer 110. Inner tubular member 102, in contrast to the prior described embodiments, includes a first reinforcement layer 112 and a second reinforcement layer 114, where the first reinforcement layer provides greater stiffness or column strength than does the second reinforcement layer 114. Preferably, the first reinforcement layer 112 will be formed as a braided ribbon structure. The second reinforcement layer 112, in contrast, will preferably be a helically wound ribbon, where the individual turns of the ribbon are axially spaced-apart by a short distance to enhance flexibility. Usually, the ribbon of the second reinforcement layer 114 will be a stainless steel ribbon. Also, the second reinforcement layer 114 will usually extend fully to the distal end 120 of the inner catheter 102.

Figure 4:
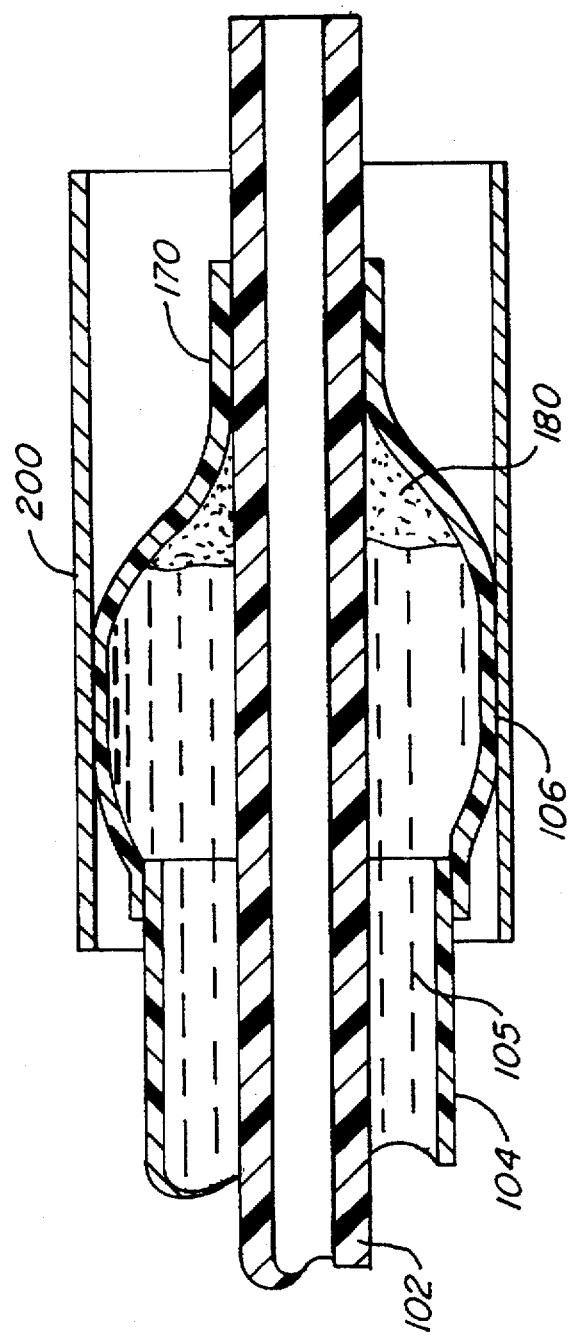

The outer tubular member 104 will preferably be reinforced, typically by a helically wound ribbon, such as a stainless steel ribbon having cross-sectional dimensions of about 0.001 inch by 0.005 inch. The outer tubular member 104 will typically be composed of Pebax®. The balloon is preferably highly compliant. As illustrated in FIG. 4, the balloon 106 will be attached at its proximal end to the distal end of the sheath 104 of tat its distal end to the distal end of the catheter 102. In the preferred embodiment, a separate, soft distal tip 122 will be attached to the distal end of the inner catheter 102. Usually, a radiopaque marker, such as the marker ring 124, will be embedded within the soft tip 122.

Figure 3:
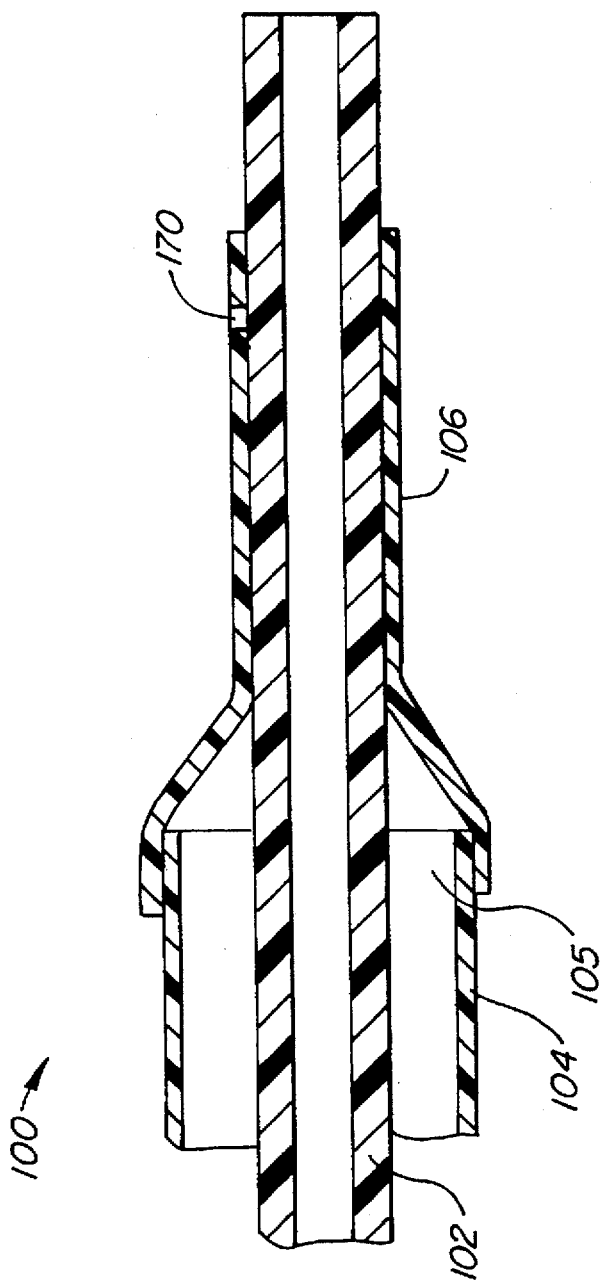
FIGS. 3–5 are simplified views showing the inflation, venting, and flushing of the catheter of FIG. 2.
Figure 5:
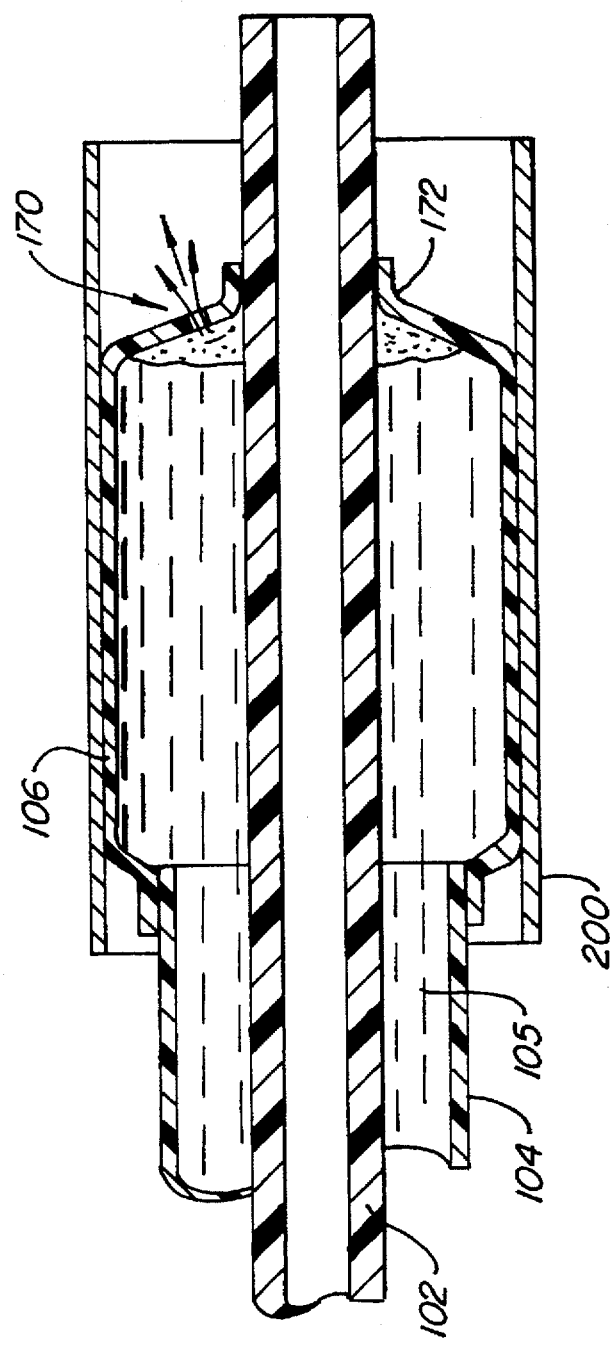

Referring now to FIGS. 3–5, preparation and flushing of the catheter 100 according to the method of the present invention will be described. In its initial configuration, as illustrated in FIG. 3, the balloon 106 is tightly constricted against the inner tubular member 102. In particular, the inner surface of vent hole 170 lies directly over the outer surface of the inner tubular member 102 so that gases are prevented from entering the interior of the balloon. Prior to use, however, the balloon 106 must be flushed to remove all gases which are already present within the catheter 100. A flushing fluid, typically saline and/or contrast medium will be introduced through the annular inflation lumen 105, as illustrated in FIG. 4. The inflation medium will begin by expanding the balloon near its proximal end, causing entrapped gases to collect in a region 180 which moves progressively toward the distal end of the balloon. During the initial stages of balloon inflation, the distal end of the balloon will remain radially closed so that the vent hole 170 is covered by the exterior surface of the inner tubular member 102.

In a preferred aspect of the present invention, a tubular constraining member 200 is placed coaxially over the exterior balloon 106. The constraining member 102 has an inner lumen diameter selected to limit radial expansion of the balloon 106 to a diameter generally equal to the normal inflation diameter of the balloon. Typically, the inner diameter of the constraining member 200 will be in the range from 25% to 100% of the nominal inflation diameter of the balloon 106.

As the balloon continues to expand, the distal end of balloon 106 will open and expose the vent hole 170, as illustrated in FIG. 5. In particular, the balloon will open about a circumferential hinge region 172 which is defined by the attachment of the balloon to the inner tubular member 102. The gases will flow out through the vent hole 170, as illustrated by the arrows in FIG. 5., usually the flushing will continue until all of the gases have passed through the vent 170 and optionally until a small portion of the inflation medium also passes through the expanded vent hole. The particular advantage of the present invention is that the vent holes which are formed in the elastomeric membrane will have the ability to expand beyond their cross-sectional area when the balloon is uninflated. In particular, by use of the constraining 200, the balloon 106 can be inflated well over its normal inflation pressure, further opening the vent hole 70 to permit a greater rate of gas and liquid flushing.

After the flushing is complete, the inflation medium will be removed from the balloon (typically by drawing a vacuum from the interior of the catheter), and the balloon will collapse back to the configuration shown in FIG. 3 where the vent hole is effectively sealed to inhibit re-entry of gases into the interior of the balloon or elsewhere in the catheter. Thus, the balloon catheter 100 has now been flushed with liquid so that it may be used without risk of air embolisms.

The invention has now been explained with reference to specific embodiments. Other embodiments will be apparent to those of ordinary skill in the art upon reference to this disclosure. It is therefore not intended that this invention be limited, except as indicated by the appended claims.

What is claimed is:

1. A balloon catheter comprising a catheter body having a proximal end, a distal end, and at least one inflation lumen therethrough; and an elastomeric balloon disposed over the distal end of the catheter body to receive inflation medium from the inflation lumen, said balloon comprising an elastomeric membrane having at least one vent hole therethrough.

2. A balloon catheter as in claim 1, wherein the vent hole is disposed near the distal end of the balloon.

3. A balloon catheter as in claim 2, wherein the elastomeric balloon when uninflated is constricted over the catheter body so that the vent hole is covered by the catheter body.

4. A balloon catheter as in claim 3, wherein the inflation lumen opens into a proximal end of the balloon, wherein inflation of the balloon causes progressive expansion of the balloon from the proximal end to the distal end so that gas within the balloon will be moved distally toward the vent hole.

5. A balloon catheter as in claim 1, wherein the elastomeric membrane is composed of a material selected from the group comprising latex, silicone rubber, and polyurethane.

6. A balloon catheter as in claim 5, wherein the elastomeric membrane has a thickness in the range from 0.025 mm to 0.25 mm.

7. A balloon catheter as in claim 6, wherein the hole has a maximum width of 0.25 mm when the balloon is uninflated.

8. A balloon catheter as in claim 7, wherein the hole has a width in the range from 0 mm to 0.25 mm when the balloon is uninflated.

9. A balloon catheter as in claim 8, wherein the hole has a width in the range from 0.01 mm to 0.5 mm when the balloon is inflated to a pressure of 0.5 atm.

10. An inflation system comprising:

a balloon catheter as in claim 1; and a tubular constraint having a lumen which receives the elastomeric balloon and contains inflation thereof.

11. A balloon catheter comprising:

a catheter body having a proximal end, a distal end, and at least one inflation lumen therethrough;

an elastomeric balloon having a proximal end and a distal end, wherein the proximal and distal ends are circumferentially attached over the catheter body to define spaced-apart hinge regions as the balloon is inflated and wherein a vent hole is disposed in the balloon immediately adjacent the distal hinge region, so that inflation of the balloon deflects the balloon near the distal hinge region to open the vent hole.

12. A balloon catheter as in claim 11, wherein the catheter body includes an inner tubular member and an outer tabular member received over the inner tubular member, wherein the annular inflation lumen is formed therebetween.

13. A balloon catheter as in claim 12, wherein the proximal end of the elastomeric balloon is attached near the distal end of the outer tubular member and wherein the distal end of the elastomeric balloon is attached near the distal end of the inner tubular member.

14. A balloon catheter as in claim 11, wherein the inflation lumen opens into a proximal end of the balloon, wherein inflation of the balloon causes progress expansion of the balloon from the proximal end to the distal end so that gas within the balloon will be moved distally toward the vent hole.

15. A balloon catheter as in claim 14, wherein the elastomeric membrane is composed of a material selected from the group comprising latex, silicone rubber, and polyurethane.

16. A balloon catheter as in claim 15, wherein the elastomeric membrane has a thickness in the range from 0.025 mm to 0.25 mm.

17. A balloon catheter as in claim 16, wherein the hole has a maximum width of 0.25 mm when the balloon is uninflated.

18. A balloon catheter as in claim 17, wherein the hole has a width in the range from 0 mm to 0.25 mm when the balloon is uninflated.

19. A balloon catheter as in claim 18, wherein the hole has a width in the range from 0.01 mm to 0.5 mm when the balloon is inflated to a pressure of 0.5 atm.

20. An inflation system comprising:
    a balloon catheter as in claim 11; and
    a tubular constraining member having a lumen which receives the elastomeric balloon and contains inflation thereof.

21. An improved balloon catheter of the type comprising a catheter body, a self-venting balloon on the catheter body, wherein the improvement comprises a balloon formed at least in part from an elastomeric membrane and having at least one vent hole through said elastomeric membrane.

22. An improved balloon catheter as in claim 21, wherein the improvement further comprises a vent hole which expands as the balloon is inflated.

23. An improved balloon catheter as in claim 22, where the vent hole has a maximum width in the range from 0 mm to 0.25 mm when the balloon is uninflated and a maximum width in the range from 0.01 mm to 0.5 mm when the balloon is inflated to 0.5 atm.

24. A method for venting an elastomeric balloon catheter, said method comprising:
    providing a balloon catheter having an elastomeric balloon with a vent hole therein; and
    inflating the balloon with a liquid medium to resiliently expand the balloon and vent gasses trapped in the balloon through the vent hole.

25. A method as in claim 24, wherein the vent hole is disposed near the distal end of the balloon and wherein the balloon is inflated so that it progressively opens from the proximal end to the distal end to cause entrapped gases to move toward the vent.

26. A method as in claim 24, wherein the cross-sectional area of the vent hole increases as it expands.

27. A method as in claim 24, wherein the elastomeric balloon is inflated with a lumen of a tubular constraining member to enhance venting of the gases.

28. A method as in claim 27, wherein the tubular lumen has a diameter which is from 25% to 100% of a nominal maximum inflation diameter of the balloon.

29. A method as in claim 24, wherein the balloon is inflated to a pressure in the range from 1 psi to 60 psi.

30. A method as in claim 24, wherein the balloon is inflated with a liquid volume from 0.03 ml to 0.15 ml.

* * * * *